(12) United States Patent
Colvin et al.

(10) Patent No.: US 6,498,884 B1
(45) Date of Patent: Dec. 24, 2002

(54) WIDE-VIEW ENDOSCOPE COMPATIBLE WITH HDTV FORMAT

(75) Inventors: Stephen B. Colvin, New York, NY (US); Eugene Grossi, New York, NY (US); Alan Katz, Freeport, NY (US)

(73) Assignee: Quickie Vision LLC, New York, NY (US)

( * ) Notice: Subject to any disclaimer, the term of this patent is extended or adjusted under 35 U.S.C. 154(b) by 28 days.

(21) Appl. No.: 09/691,988

(22) Filed: Oct. 19, 2000

Related U.S. Application Data

(60) Provisional application No. 60/160,662, filed on Oct. 21, 1999.

(51) Int. Cl.[7] .................................................. G02B 6/06
(52) U.S. Cl. ....................................... 385/117; 600/160
(58) Field of Search ........................... 385/117; 600/138, 600/160, 920

(56) References Cited

U.S. PATENT DOCUMENTS

| | | | |
|---|---|---|---|
| 2,975,785 A | 3/1961 | Sheldon | |
| 3,525,561 A | 8/1970 | Takahashi | |
| 4,369,768 A | 1/1983 | Vukovic | |
| 4,702,571 A | 10/1987 | Barber | |
| 4,872,740 A | 10/1989 | Terada et al. | |
| 4,918,521 A | 4/1990 | Yabe et al. | |
| 4,947,245 A | * 8/1990 | Ogawa et al. | 385/98 |
| 4,979,498 A | * 12/1990 | Oneda et al. | 128/6 |
| 5,494,483 A | 2/1996 | Adair | |
| 5,630,784 A | 5/1997 | Siegmund et al. | |
| 5,630,788 A | * 5/1997 | Forkner et al. | 600/182 |
| 6,011,889 A | * 1/2000 | Daniel et al. | 385/117 |
| 6,099,466 A | * 8/2000 | Sano et al. | 600/160 |

\* cited by examiner

*Primary Examiner*—Tulsidas Patel
*Assistant Examiner*—Thanh-Tam Le
(74) *Attorney, Agent, or Firm*—Greenberg Traurig, LLP; Todd S. Sharinn

(57) ABSTRACT

A wide-view endoscope comprising a rounded body having an inner surface, a proximal end and a distal end, at least one lens element having an outer surface, a plurality of gaps formed by the inner surface of the body and the outer surface of the lens element, where at least one of the gaps is disproportionate in size by comparison to the remaining gaps, and at least one conduit for the transmission of light from an external light source to a visualized object, the conduit being disposed of in the gaps. Whereby, light is asymmetrically transmitted to the visualized object and the visualized object has a three-dimensional appearance that is produced through the shadowing resulting from the asymmetric transmission of light to the visualized object.

8 Claims, 3 Drawing Sheets

WIDE-VIEW ENDOSCOPE COMPATIBLE WITH HDTV FORMAT

CROSS REFERENCE TO RELATED UNITED STATES APPLICATIONS

This application is a continuation of the provisional application Serial No. 60/160,662 filed Oct. 21, 1999.

FIELD OF THE INVENTION

The present invention relates to a wide-view endoscope compatible with high definition television ("HDTV") format. More particularly, the present invention relates to a HDTV compatible endoscope for use in minimally invasive surgical procedures.

BACKGROUND OF THE INVENTION

Traditionally endoscopes were of the rigid "rod-lens" type, utilizing a series of lenses to relay the image of an object from a distal end to a proximal eyepiece or other viewing means. Such a device is taught in U.S. Pat. No. 4,168,882, whose disclosure is incorporated herein by reference. In that device, the image of an object area is formed by a first distal lens. A second lens re-images the first image to a third lens, which re-images the second image to a fourth lens, and so on, until the image is relayed to the viewing means. Such devices are generally plagued by the need for repeated maintenance and poor maneuverability.

The use of fiber optic, multifilament and optical fiber bundles, in connection with the transmission of image light is well known in the art. The inclusion of such optics in an endoscope capable of transmitting a sufficient quantity of light to the dark field of vision is disclosed, and incorporated herein by reference, in U.S. Pat. No. 4,872,740. This endoscope, while providing greater maneuverability, and lower maintenance, is very expensive and provides limited picture quality.

An improved endoscope, for remotely examining cavities, utilizing a solid transparent high refractive index tunnel rod, in place of the conventional series of lenses, for conducting image light from a distal end to a proximal end of the device is taught, and incorporated herein by reference, in U.S. Pat. No. 5,630,784. In that device, an enhanced image is provided in a more costly manner through minimizing veiling glare and reducing contrast of the image through the development and inclusion of a high refractive index tunnel rod. This tunnel rod both shortens the apparent distance from the proximal to the distal end by virtue of its refractive index being greater than that of air, and provides a light tunnel which can transmit image light over a relatively long distance without veiling energy from wallscatter or by virtue of its lightly refractive inside walls. Despite this great leap forward, surgeons, particularly those involved in minimally invasive and endoscopic procedures are faced with the dilemma of operating on three-dimensional patients while viewing standard two-dimensional images on their monitor. They are deprived under such circumstances from the benefits of depth perception, as well as from the opportunity to effectively differentiate the targeted organs and tissue from their surroundings.

In addition, as depicted in FIGS. 2 and 3, traditional endoscopes, when used in combination with monitors, either increase magnification to oversize the image, or increase the optic field size by decreasing magnification. In either case, the Surgeon's view suffers through either a reduction of her optic field or increased vignetting, respectively. These quandaries are exacerbated when traditional endoscopes are combined with HDTV cameras, since HDTV provides, in addition to greater resolution, a wider format through an aspect ratio of 16:9. Further, as provided above, traditional endoscopes are neither efficient in the use of the entire optical path, nor capable of providing sufficient imaging to leverage the benefits provided through utilizing the HDTV equipment and format.

SUMMARY OF THE INVENTION

Therefor, it is an object of the present invention to provide an improved endoscope that provides a sharper, more focused picture having a wider field of view, while providing enhanced depth perception, without generating vignetting.

It is a further object of the present invention to provide a wide-view endoscope that incorporates a HDTV camera and is compatible with HDTV format. By using the same aspect ratio as the HDTV camera and HDTV imager, the present invention will transmit the entire optical path thus filling the full screen and providing the surgeon with an increased optical field. In addition, the HDTV format will greatly improve resolution, and ensure that the surgeon will have sufficient picture definition to delineate fine details and shadowing.

It is still a further object of the present invention to provide surgeons an effective and useful means of performing minimally invasive and endoscopic procedures previously prevented as a result of the limited resolution, poor maneuverability and the generation of vignetting by prior art endoscopes.

The present invention is directed to a wide-view endoscope that incorporates a HDTV camera and is HDTV compatible. This invention combines rectangular shaped lens elements and a differential light source. The rectangular shaped lens elements ensure that the lens pathway is fully mapped to wide format image detector of the HDTV camera. The sides of the lens elements are coated or blackened to limit glare and refractive errors. Further, the rectangular lens elements naturally form asymmetric gaps, which surround the lens element and provide a pathway for inclusion of the illuminating conduits, within the generally round endoscope body. The overall affect achieved through this orientation, is the maximization of the optical conduit by matching the shape of the lens package to that of the detector (HDTV camera chip), without increasing the outside diameter of the endoscope.

Shadowing is produced through the placement of the illuminating conduits in a non-concentric orientation. With the higher resolution and increased signal bandwidth achievable with a HDTV camera, the object shadowing will provide enhanced depth perception. This is particularly advantageous, in minimally invasive procedures, since the surgeon will gain a significantly better view of the surface she is working on, while requiring less space through the reduced diameter of the present invention. In turn, this will facilitate the surgeon's maneuvering of her instruments or the endoscope in a smaller space then traditionally required with such minimally invasive procedures, while permitting her to access and view tissues which traditional endoscopes could not reach.

DETAILED DESCRIPTION OF THE PREFERRED EMBODIMENTS

Figure 1:
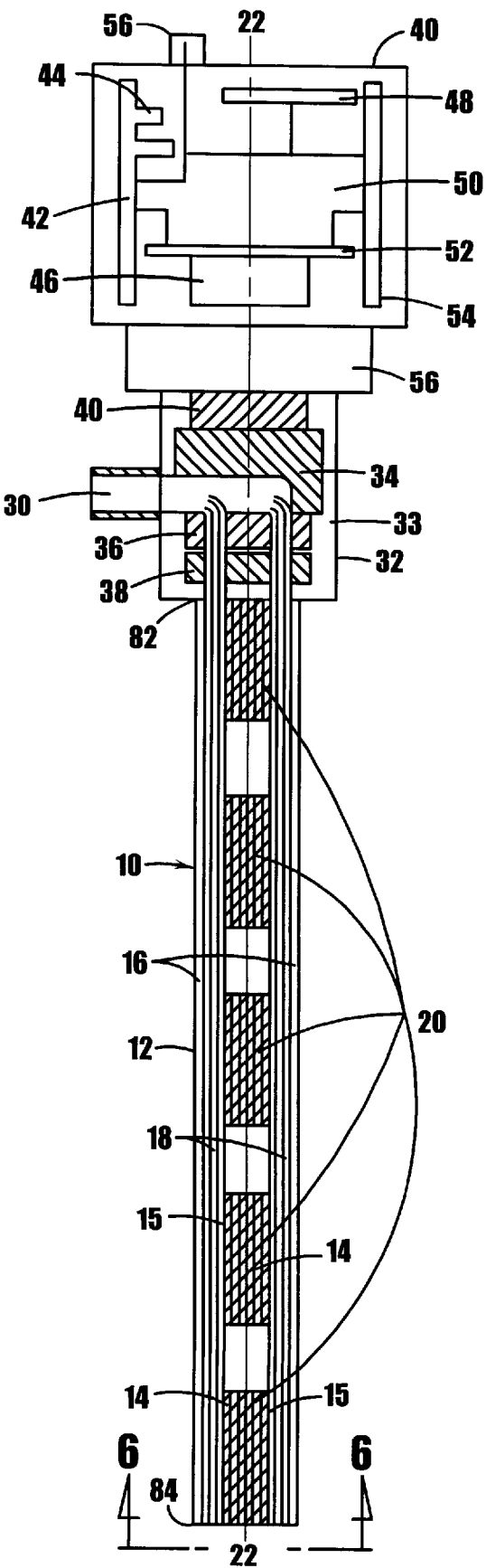
FIG. 1 is a sectional view of an endoscope according to a preferred embodiment of the present invention.
Figure 2:
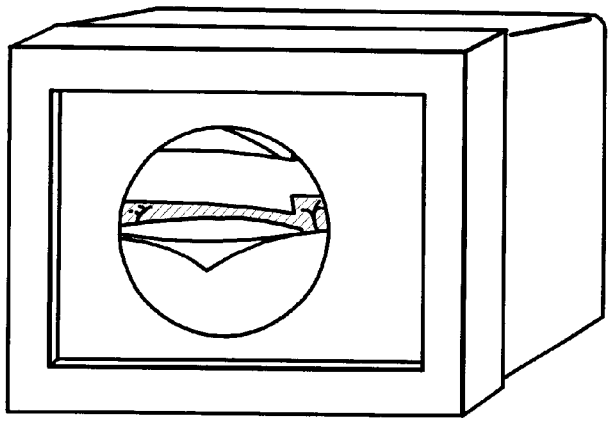
FIG. 2 is a view of a television image produced by a prior art endoscope.
Figure 3:
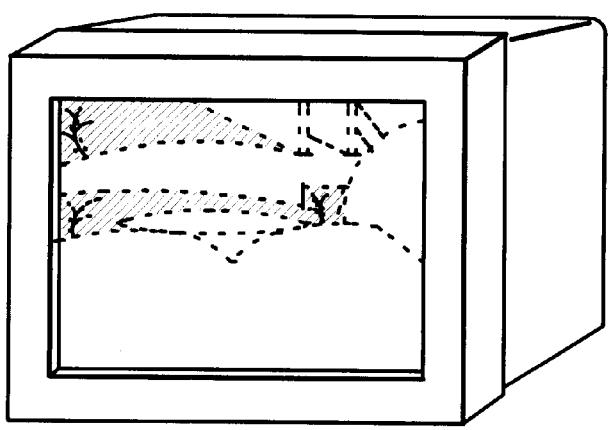
FIG. 3 is a view of a television image produced by a prior art endoscope.
Figure 4:
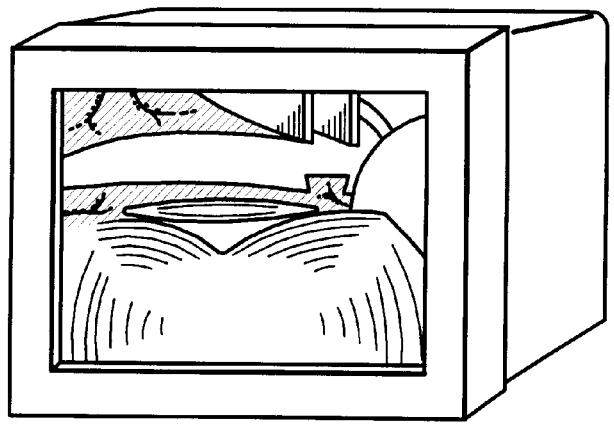
FIG. 4 is a view of an HDTV image produced by an endoscope according to a preferred embodiment of the present invention.
Figure 5:
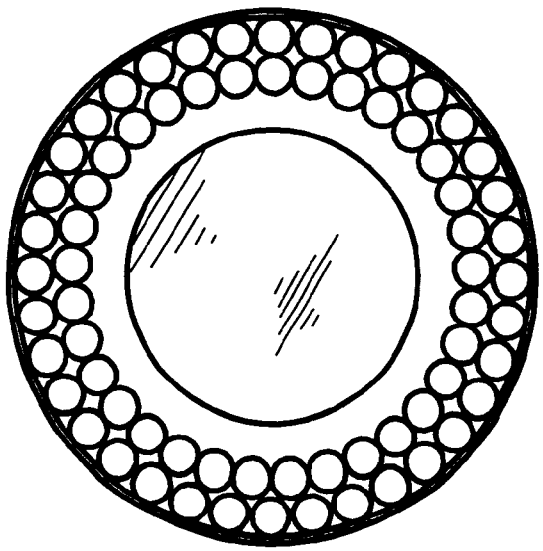
FIG. 5 is a cross-section view of a prior art endoscope illustrating the symmetric packing of the lighting elements therein.

FIG. 1 depicts the HDTV compatible endoscope 10 of the present invention, having particular utility with minimally invasive surgical procedures. As illustrated by FIG. 4, the endoscope of the present invention provides a sharper, more focused picture having a wider field of view, while providing enhanced depth perception, without generating vignetting. More specifically, by using the same aspect ratio as the HDTV camera and HDTV imager, the present invention transmits the entire optical path.

The lens system will consist of multiple lens rods 14 bundled together within the endoscope body 12 forming rectangular lens elements 20. The sides 15 of each lens rod 14 is coated or blackened, using well-known techniques, to limit glare and refractive errors. The lens rods 14 may be solid with multiple lens or may consist of multiple fibers of a single lens which would enable flexibility along the longitudinal axis of the endoscope. The lens system will preferably have sufficient optical resolution to maintain the image quality for such a wide field. Specifically, the optics will most preferably be calibrated to clearly transmit an image with a resolution of 0.01 mm.

Figure 6:
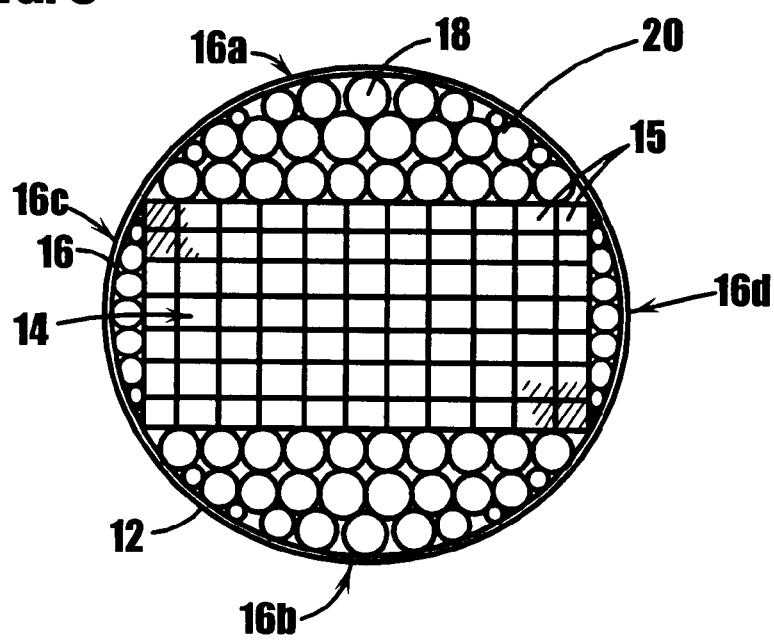
FIG. 6 is a directional view of the endoscope according to a preferred embodiment of the present invention taken on line 6—6 in FIG. 1.

Transmission of the entire optical path is accomplished through using sets of lens elements 20. Contrary to typical lens elements, the lens element of the present invention has generally rectangular shape along its latitudinal axis. These rectangular shaped elements, as depicted in FIG. 6, are preferably created by grinding oversized image rods along their longitudinal axis 22 to eliminate the opportunity for any lens pathway not precisely mapped to the wide format image detector. As illustrated by FIGS. 1 and 6, once positioned within the generally round endoscope body 12, these rectangular lens elements 20 form gaps 16 within the endoscope body 12. Such gaps 16 provide, through the inclusion of illuminating conduits 18, for a pathway to illuminate the surface under examination.

Light is delivered from the light source, through gaps 16 by illuminating conduits 18, which run along longitudinal axis 22. The light source is connected to conduits 18 by light source connector 30. Light source connector 30 is housed within lens housing 32 along with focusing lens 34, magnification lens 36, objective lens 38, and eyepiece lens 40. Each lens rod 14 sequentially receives an image from its objective end and transmits the image to its dital end. Lens assembly 33, which comprises lenses 34, 36, 38 and 40, magnifies and focuses the image transmitted by the lens rods 14 onto imaging chip 46. Lens assembly 33 is optimized for 16:9 aspect ratio, thus reducing the vignetting in a horizontal plane.

A high resolution HDTV compatible camera is used to capture and transmit the image, over cable 56, as depicted in FIG. 1, from the endoscope to a HDTV monitor. The camera system will have at least 2 million imaging pixels, which will preferably be equivalent to the resolution of the endoscope lens system. By comparison, conventional camera systems (having a 4:3 aspect ratio with approximately 380,000 pixels) which would provide insufficient pixel density to ensure enough definition to delineate fine details and shadowing with a wide-angle view.

The present embodiment, as depicted in FIG. 1, HDTV 40 is mounted on the proximal end 82 of the endoscope body. HDTV 40 comprises PC board 42 with video amplifiers 44, charge couple device (CCD) imaging chip 46, prism block assembly 50, and PC boards 48, 52 and 54. A cable 56 transmits the HDTV signal from HDTV 40 to a monitor (not depicted).

In a preferred embodiment of the present invention, the endoscope body, which is an elongated hollow structure having a proximal end 82 and a distal end 84, will remain generally round. Gaps 16a and 16b, located above and below the rectangular lens element 20 respectively, may be of equal or varying size with respect to one another. However, gaps 16a and/or 16b will always vary in size with reference to gap(s) 16c and/or 16d. This orientation ensures a non-concentric lighting pathway and the delivery of asymmetric light to the visualized image. By placing a disproportionate number of illuminating conduits 18 around the various sides of image pathway 14, formed by lens element 16, shadowing is produced through the asymmetric lighting of the visualized object. Complimented by the higher resolution and increased signal bandwidth achievable with a HDTV camera, the object shadowing will provide enhanced depth perception.

In an alternate preferred embodiment, an eyepiece lens 40 is incorporated into the endoscope. In this embodiment, the camera system may contain an eyepiece coupler 56 and focusing lenses 34 at the appropriate focal lengths to match the lens system of the endoscope. If no eyepiece is present on the endoscope, the focusing mechanism will preferably be internal to the scope (adjustable focusing lens) with a mechanical coupler to the endoscope.

The overall affect achieved through this orientation, is the maximization of the optical conduit by matching the shape of the lens package to that of the detector (HDTV camera chip), without increasing the outside diameter of the endoscope. This is particularly advantageous, in minimally invasive procedures, since the surgeon will gain a significantly better view of the surface she is working on, while requiring less space through the reduced diameter of the present invention. This reduction in width and girth of the present endoscope will facilitate the surgeon's maneuvering of her instruments or the endoscope in a smaller space then traditionally required by minimally invasive or endoscopic procedures, while permitting her to access and view tissues which traditional endoscopes could not reach.

In another preferred embodiment of this invention, the light source near the objective end of the endoscope is hingedly secured. Once the endoscope has been inserted into the cavity to be examined, the illumination tip can swing out, away from the central access of the endoscope via a mechanical control. Prior to removing the endoscope, the illuminating tip can be folded back into the endoscope's lateral wall, returning the profile of the endoscope to its original shape. By extending the source of illumination away from the center of the optical pathway, the incident angle of the light reaching the viewing target is increased and, therefore, the shadowing achievable is also increased. This will improve the three-dimensional effect of the viewing system provided through the inclusion of the present invention.

FIG. 6 depicts still another preferred embodiment of the present invention in which the external shape of the endoscope is elliptical or ovoid in nature. However, like the prior embodiments, the lens element 14 of the present embodiment will be rectangular, and when grouped within the endoscope body, will form gaps 16 through which the illuminating conduits 18 will be placed. The elliptical or ovoid shape of this embodiment, results in heightened shadowing produced through increased asymmetry in the packing of the illuminating fibers. More particularly, the elliptical or ovoid shape permits an accentuation of the advantages and effects realized through the use of the aforementioned embodiments since the asymmetry of the lighting of the object visualized, with this embodiment, is even greater. Further, this shape will facilitate the surgeon's maneuvering of her instruments and/or the endoscope in a smaller space than traditionally required with such minimally invasive procedures, while providing the surgeon with greater access to tissues which are typically difficult or impossible to view, and higher resolution and depth perception than associated with traditional endoscopes.

In each of the above-described embodiments, the endoscope according to the present invention is used with HDTV format. However, the present invention is not restricted to the use only for endoscopes for HDTV broadcasting, it can be used in connection with still digital cameras and the like and is effective to provide the advantages described herein.

In this invention, it is apparent that working modes different in a wide range can be formed on the basis of this invention without deviating from the spirit and scope of the invention. This invention is not restricted by a specific working mode except being limited by the appended claims.

What is claimed:

1. An endoscope comprising:
   a rounded body having an inner surface, a proximal end and a distal end,
   at least one lens element having an outer surface, a longitudinal axis and a latitudinal axis, the longitudinal axis of the lens element having a first end and a second end, the first end of the longitudinal axis interfacing with an image forming optical means, and the second end of the longitudinal axis disposed for viewing objects through the distal end of the body, wherein the lens element comprises of a plurality of multifilament optical fibers bundled together along the longitudinal axis of the lens element,
   a plurality of gaps formed by the inner surface of the body and the outer surface of the lens element, whereby at least one of the gaps is disproportionate in size by comparison to the remaining gaps,
   at least one conduit for the transmission of light from a light source to a visualized object, the conduit being disposed within the gaps,
   whereby light is asymmetrically transmitted to the visualized object and the visualized object has a three-dimensional appearance that is produced through shadowing resulting from the asymmetric transmission of light to the visualized object.

2. An endoscope according to claim 1, wherein the lens element has a rectangular configuration along its latitudinal axis.

3. An endoscope according to claim 1, wherein the lens element has an ovoid configuration along its latitudinal axis.

4. An endoscope according to claim 1, wherein the lens element is constructed from multiple stacked optical rods.

5. An endoscope according to claim 1, wherein the lens element is constructed from a single optical rod.

6. An endoscope according to claim 1, wherein the lens element has a refractive periphery.

7. An endoscope according to claim 1, wherein the image forming optical means comprises:
   a high definition television camera mounted in communication with the lens element and capable of transmitting a high definition television signal, and
   a high definition television monitor for displaying the high definition television signal.

8. An endoscope according to claim 1, wherein the image forming optical means comprises:
   a digital camera, and
   a means for displaying the digital photographs produced by the digital camera.

* * * * *